(12) United States Patent
Relan et al.

(10) Patent No.: US 10,349,856 B2
(45) Date of Patent: Jul. 16, 2019

(54) METHODS AND SYSTEMS FOR MAPPING CARDIAC RESTITUTION

(71) Applicant: St. Jude Medical, Cardiology Division, Inc., St. Paul, MN (US)

(72) Inventors: Jatin S. Relan, Bordeaux (FR); Valtino X. Afonso, Oakdale, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/766,289

(22) PCT Filed: Sep. 29, 2016

(86) PCT No.: PCT/US2016/054281
§ 371 (c)(1),
(2) Date: Apr. 5, 2018

(87) PCT Pub. No.: WO2017/062248
PCT Pub. Date: Apr. 13, 2017

(65) Prior Publication Data
US 2018/0279895 A1    Oct. 4, 2018

Related U.S. Application Data

(60) Provisional application No. 62/238,451, filed on Oct. 7, 2015.

(51) Int. Cl.
*A61B 5/044*    (2006.01)
*A61B 5/04*    (2006.01)
(Continued)

(52) U.S. Cl.
CPC .......... *A61B 5/044* (2013.01); *A61B 5/04012* (2013.01); *A61B 5/0422* (2013.01);
(Continued)

(58) Field of Classification Search
None
See application file for complete search history.

(56) References Cited

U.S. PATENT DOCUMENTS 5,697,377 A    12/1997    Wittkampf
5,983,126 A    11/1999    Wittkampf
(Continued)

FOREIGN PATENT DOCUMENTS

WO    2012/097059    7/2012

OTHER PUBLICATIONS

International Search Report and Written Opinion for PCT/US2016/054281, dated Nov. 21, 2016.

*Primary Examiner* — Michelle Chin
(74) *Attorney, Agent, or Firm* — Wiley Rein LLP

(57) ABSTRACT

A method of mapping cardiac restitution includes: receiving a plurality of EP data points including location and restitution data; identifying a subset of the EP data points forming an EP data point cluster; fitting a restitution curve to the restitution data of the EP data points forming the cluster; and identifying at least one restitution metric for a region of the cardiac surface corresponding to the cluster from the restitution curve. The restitution curve can be an exponential function using quiescent interval data (e.g., DI and/or CL) as the independent variable and cardiac repolarization activity data (e.g., APD, ARI, and/or EGM width) as the dependent variable. The parameters of the exponential function can be determined by optimizing a cost function. A graphical representation of the restitution metric can also be output on a three-dimensional model of the cardiac surface.

20 Claims, 6 Drawing Sheets

(51) Int. Cl.
  *G16H 15/00*  (2018.01)
  *G06T 11/20*  (2006.01)
  *A61B 5/00*  (2006.01)
  *A61B 5/042*  (2006.01)

(52) U.S. Cl.
  CPC ............ *A61B 5/743* (2013.01); *G06T 11/206* (2013.01); *G16H 15/00* (2018.01); *G06T 2210/41* (2013.01)

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2013/0006131 A1 | 1/2013 | Narayan et al. |
| 2014/0187989 A1 | 7/2014 | Thakur et al. |

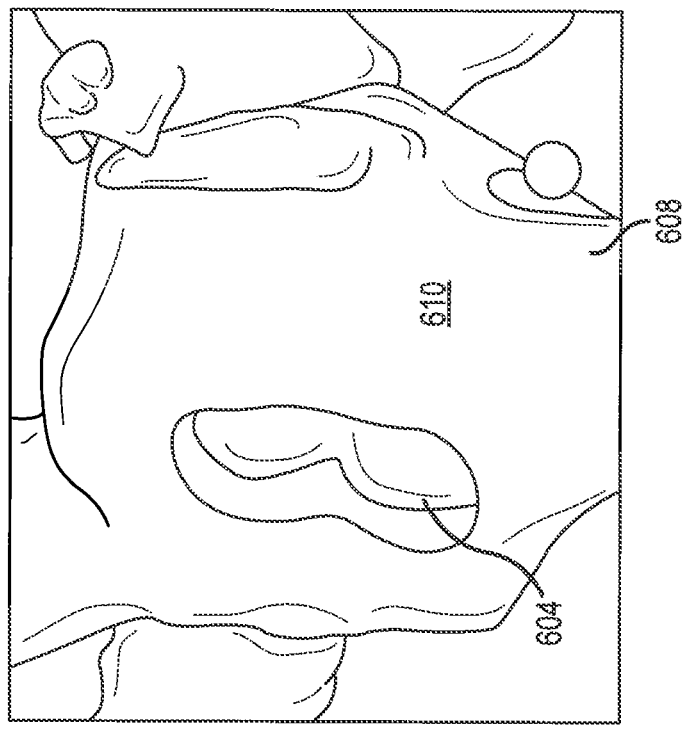
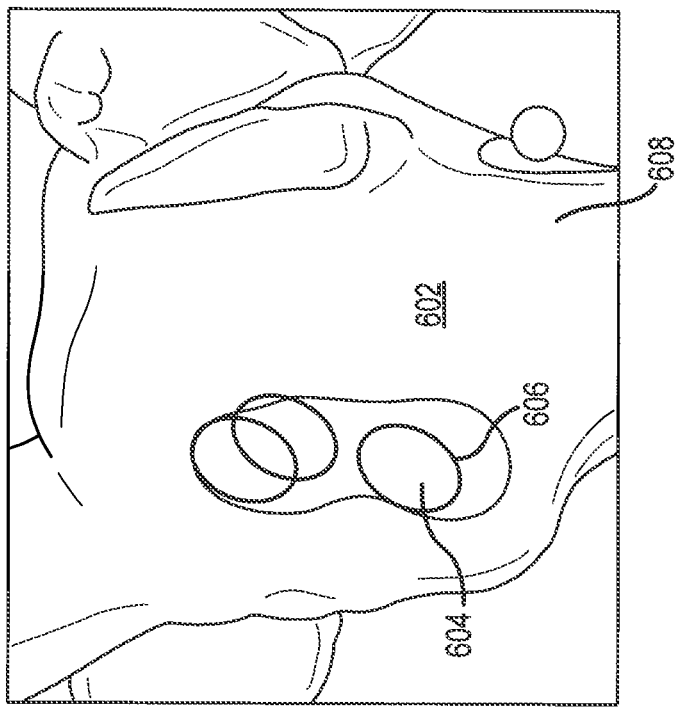

METHODS AND SYSTEMS FOR MAPPING CARDIAC RESTITUTION

CROSS-REFERENCE TO RELATED APPLICATIONS

This application claims the benefit of U.S. provisional application No. 62/238,451, filed 7 Oct. 2015, which is hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for mapping cardiac restitution.

"Restitution" refers to a functional relationship between the duration of a cardiac action potential and the length of the quiescent interval preceding it. In many cases, this relationship reflects limited change in action potential duration ("APD") over a broad range of long diastolic intervals ("DI") and shortening of the APD at shorter DIs. APD restitution can therefore be thought of as a form of adaptation to changes in heart rate.

An APD restitution curve can be constructed by varying the DI and plotting the resulting APD. To the first order, an APD restitution curve reflects the underlying dynamics of the system during steady-state conditions. For APD restitution curves with steep slopes (i.e., greater than one), small changes in DI result in large changes in APD. On the other hand, for APD restitution curves with shallow slopes (i.e., less than one), small changes in DI are damped out over subsequent beats. Research has shown that steep restitution slopes can lead to breakup of spiral waves in tissue.

"Cardiac electrogram restitution" is an analogous functional relationship between the length of a preceding interval (e.g., cycle length or DI) and the successive duration (e.g., APD, activation recovery interval ("ARI"), or EGM width). This relationship shows a form of adaptation to changes in heart rate and studies tissue properties that control the dynamic behavior of the heart.

It would be desirable to map cardiac restitution in real time during an electrophysiology ("EP") study.

BRIEF SUMMARY

Disclosed herein is a method of mapping cardiac restitution, including the steps: receiving a plurality of electrophysiology ("EP") data points at a signal processor, each EP data point of the plurality of EP data points including location data and restitution data; receiving user input defining an anchor EP data point of the plurality of EP data points; identifying a subset of the plurality of EP data points forming an EP data point cluster about the anchor EP data point, wherein the EP data point cluster defines a region of a cardiac surface; fitting a restitution curve to the restitution data of the subset of the plurality of EP data points forming the EP data point cluster about the anchor EP data point; and identifying at least one restitution metric for the region of the cardiac surface from the restitution curve. A graphical representation of the at least one restitution metric can also be output on a three-dimensional model of the region of the cardiac surface.

The restitution data can include quiescent interval data (e.g., DI data and cycle length data) and/or cardiac repolarization activity data (e.g., APD data, ARI data, and EGM width data).

According to aspects of the disclosure, the step of identifying a subset of the plurality of EP data points forming an EP data point cluster about the anchor EP data point includes identifying a subset of the plurality of EP data points falling within a sphere centered at the anchor EP data point. The radius of the sphere can be user defined; one suitable radius is 9 mm.

In additional aspects of the disclosure, the step of fitting a restitution curve to the restitution data of the subset of the plurality of EP data points forming the EP data point cluster about the anchor EP data point includes fitting an exponential restitution curve to the restitution data of the subset of the plurality of EP data points forming the EP data point cluster about the anchor EP data point. The exponential restitution curve can be defined by the equation $y=f(x)=-a*e^{-\lambda x}+b$, wherein x is quiescent interval data, y is cardiac repolarization activity data, and a, b, and $\lambda$ are restitution parameters that can, in turn, be determined by optimizing a cost function.

One cost function, particularly suitable for use in steady-state restitution analysis, is $\min_\theta \Sigma_{j=1}^{N}(f(x^{i,j},\theta^i)-y^{i,j})^2$, wherein i designates the region of the cardiac surface; j designates the $j^{th}$ EP data point, of a total of N EP data points, defining the region i of the cardiac surface; the restitution parameters a, b, and $\lambda$ are collectively designated $\theta$; and a is between 0.1 and 1, inclusive; b is between 0 and 1, inclusive; and $\lambda$ is between 0.1 and 100, inclusive.

Another suitable cost function, particularly suitable for use in dynamic restitution analysis, is $\min_\theta \Sigma_{m=0}^{K}(f(x^{i,j,m},\theta^j)-y^{i,j,m})^2$, wherein i designates the region of the cardiac surface; j designates the $j^{th}$ EP data point defining the region i of the cardiac surface; m designates the $m^{th}$ beat, of a total of K beats, measured at the $j^{th}$ EP data point defining the region i of the cardiac surface; the restitution parameters a, b, and $\lambda$ are collectively designated $\theta$; and a is between 0.1 and 1, inclusive; b is between 0 and 1, inclusive; and $\lambda$ is between 0.1 and 100, inclusive.

It is also contemplated, particularly in the case of a steady-state restitution analysis, that the step of identifying at least one restitution metric for the region of the cardiac surface from the restitution curve can include assigning an identical restitution metric for the region of the cardiac surface to the anchor EP data point and to each EP data point of the subset of the plurality of EP data points forming the EP data point cluster about the anchor EP data point.

Also disclosed herein is a method of mapping cardiac restitution, including the steps: acquiring a plurality of EP data points, each EP data point of the plurality of EP data points including location data, quiescent interval data, and cardiac repolarization activity data; inputting the plurality of EP data points to a signal processor, and, using the signal processor: identifying a subset of the plurality of EP data points forming an EP data point cluster; fitting a restitution curve to the quiescent interval data and the cardiac repolarization activity data of the subset of the plurality of EP data points forming the EP data point cluster; and identifying at least one restitution metric for the EP data point cluster using the restitution curve; and outputting a graphical representation of the identified at least one restitution metric for the EP data point cluster on a three-dimensional model of a region of a cardiac surface including the EP data point cluster.

The step of fitting a restitution curve to the quiescent interval data and the cardiac repolarization activity data of the subset of the plurality of EP data points forming the EP data point cluster can include fitting an exponential function using the quiescent interval data as the independent variable of the exponential function and the cardiac repolarization activity data as the dependent variable of the exponential function.

The step of outputting a graphical representation of the identified at least one restitution metric for the EP data point cluster on a three-dimensional model of a region of a cardiac surface including the EP data point cluster can include outputting a single graphical representation over an entirety of the region of the cardiac surface including the EP data point cluster. This is particularly suitable for steady-state restitution analysis.

The step of identifying at least one restitution metric for the EP data point cluster using the restitution curve can include identifying one or more of a maximum slope of the restitution curve and an asymptotic limit of the restitution curve.

In other aspects of the disclosure, a system for mapping cardiac restitution includes a cardiac restitution analysis processor configured: to receive a plurality of EP data points, each EP data point of the plurality of EP data points including location data and restitution data, the restitution data including quiescent interval data and cardiac repolarization activity data; to identify a subset of the plurality of EP data points forming an EP data point cluster; to fit a restitution curve to the restitution data of the subset of the plurality of EP data points forming the EP data point cluster; and to identify at least one restitution metric for the EP data point cluster from the restitution curve. The system can also optionally include a mapping processor configured to generate and output a graphical representation of the at least one restitution metric for the EP data point cluster on a three-dimensional representation of a portion of a cardiac surface including the EP data point cluster.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 6A is a representative restitution map according to the teachings herein resulting from a steady-state restitution protocol.

FIG. 6B is a representative restitution map according to the teachings herein resulting from a dynamic restitution protocol.

DETAILED DESCRIPTION

The present disclosure provides methods, apparatuses, and systems the creation of electrophysiology ("EP") maps (e.g., electrocardiographic maps) including cardiac restitution data. The ordinarily skilled artisan will be familiar with EP mapping generally, such that aspects thereof will only be described herein to the extent necessary to understand the cardiac restitution maps disclosed herein.

For purposes of illustration only, therefore, aspects of the cardiac restitution mapping techniques disclosed herein will be described with reference to cardiac restitution analysis and cardiac restitution maps based on APD as a function of DI. It should be understood, however, that these teachings can be extended by analogy to other metrics. For example, cycle length ("CL") can be used instead of DI as the independent variable, while ARI and/or EGM width can be used instead of APD as the dependent variable.

The term "quiescent interval data" is used herein to refer to the independent variable in a cardiac restitution analysis, such as DI and/or CL. The term "cardiac repolarization activity data" is used herein to refer to the dependent variable in a cardiac restitution analysis, such as APD, ARI, and/or EGM width. Representative methods, systems, and apparatus for measuring and mapping DI, APD, and/or ARI are described in U.S. provisional application No. 62/238,323, filed 7 Oct. 2015, which is hereby incorporated by reference as though fully set forth herein. The term "restitution data" (or "cardiac restitution data") is used herein to refer collectively to quiescent interval data and cardiac repolarization activity data.

Various clinical protocols are known for measuring cardiac restitution. In a dynamic restitution protocol, for example, the heart is paced at a given CL until steady-state is reached, with APD and DI recorded for the duration. The process is then repeated with other CLs.

Another known clinical protocol is a steady-state (S1-S2) restitution protocol. In this protocol, the heart is paced at a fixed CL (S1) until steady-state is reached. Once steady-state is reached, the pacing is perturbed by a stimulus (S2) after waiting for a variable-length interval. The heart is then again paced at the fixed CL (S1) until steady-state is again reached, and pacing is perturbed by a different stimulus (S2). This allows the DIs and APDs resulting from the application of various stimuli (S2) to be recorded.

Via application of the foregoing protocols, or any other suitable protocol, a restitution curve can be constructed by varying DI and plotting the resulting APD. More particularly, a cardiac restitution curve can be constructed by varying the length of the preceding quiescent interval and plotting the duration of the successive cardiac repolarization activity. The restitution curve can then be constructed by fitting an exponential curve, or any other suitable curve, to the resultant data points.

Figure 1:
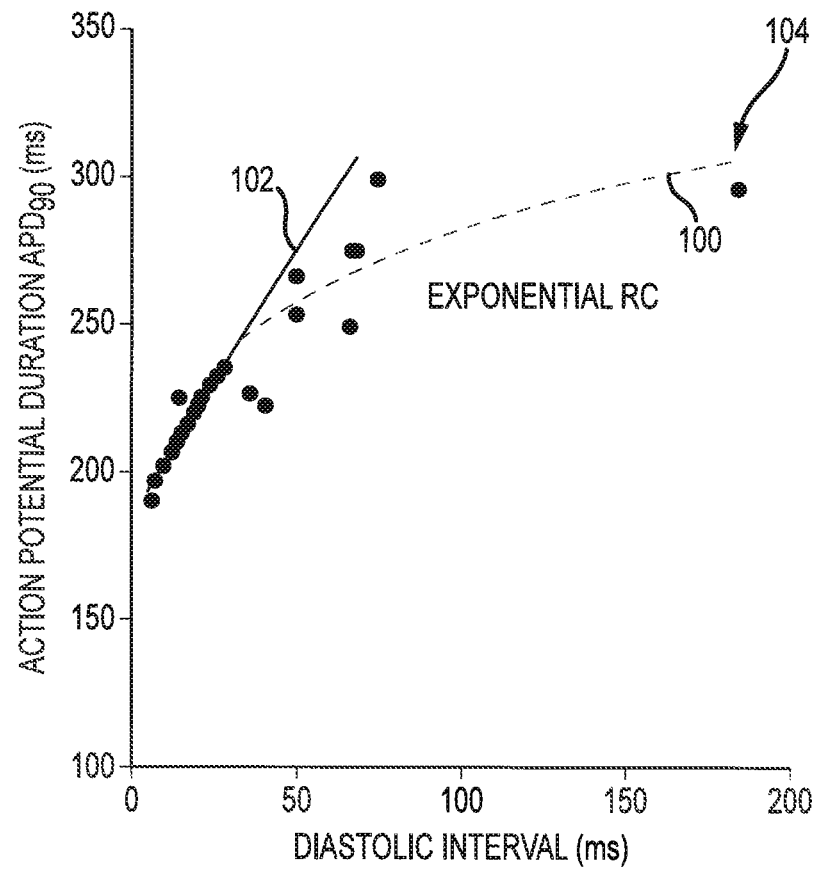
FIG. 1 is a representative restitution curve.

A representative restitution curve 100 is shown in FIG. 1. The form of restitution curve 100 reveals certain valuable information, including maximum slope 102 and asymptotic limit 104. These are referred to herein as "restitution metrics." The instant disclosure advantageously provides methods, systems, and apparatus for mapping restitution metrics in real time (that is, during the course of an EP study).

Figure 2:
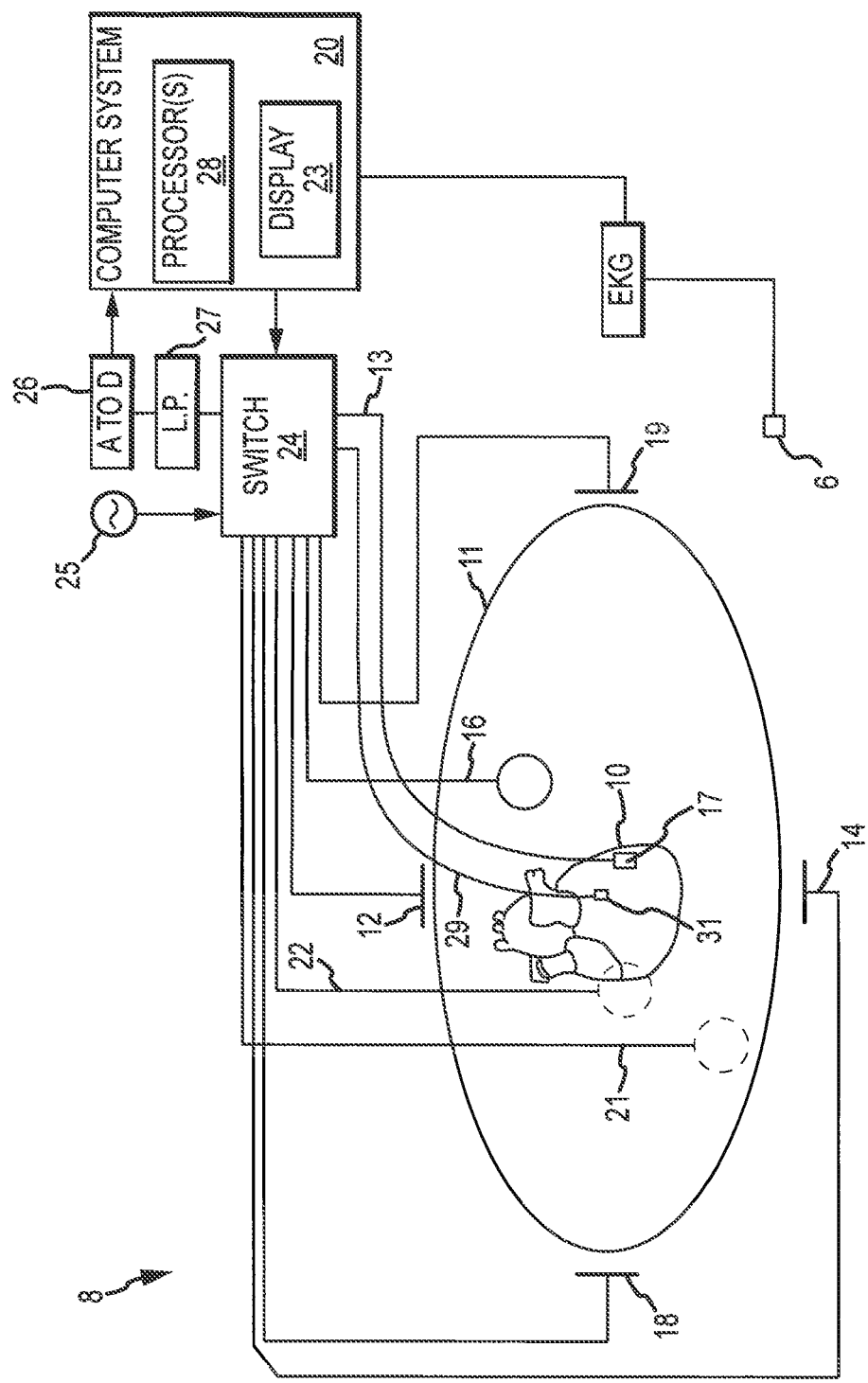
FIG. 2 is a schematic of an electrophysiology system, such as may be used in an electrophysiology study.

FIG. 2 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body or on an external frame.

In FIG. 2, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 2.

A representative catheter 13 having at least one electrode 17 (e.g., a distal electrode) is also depicted in schematic fashion in FIG. 2. This representative catheter electrode 17 can be referred to as a "measurement electrode" or a "roving electrode." Typically, multiple electrodes on catheter 13, or on multiple such catheters, will be used. In one embodiment, for example, system 8 may utilize sixty-four electrodes on twelve catheters disposed within the heart and/or vasculature of the patient.

In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 3:
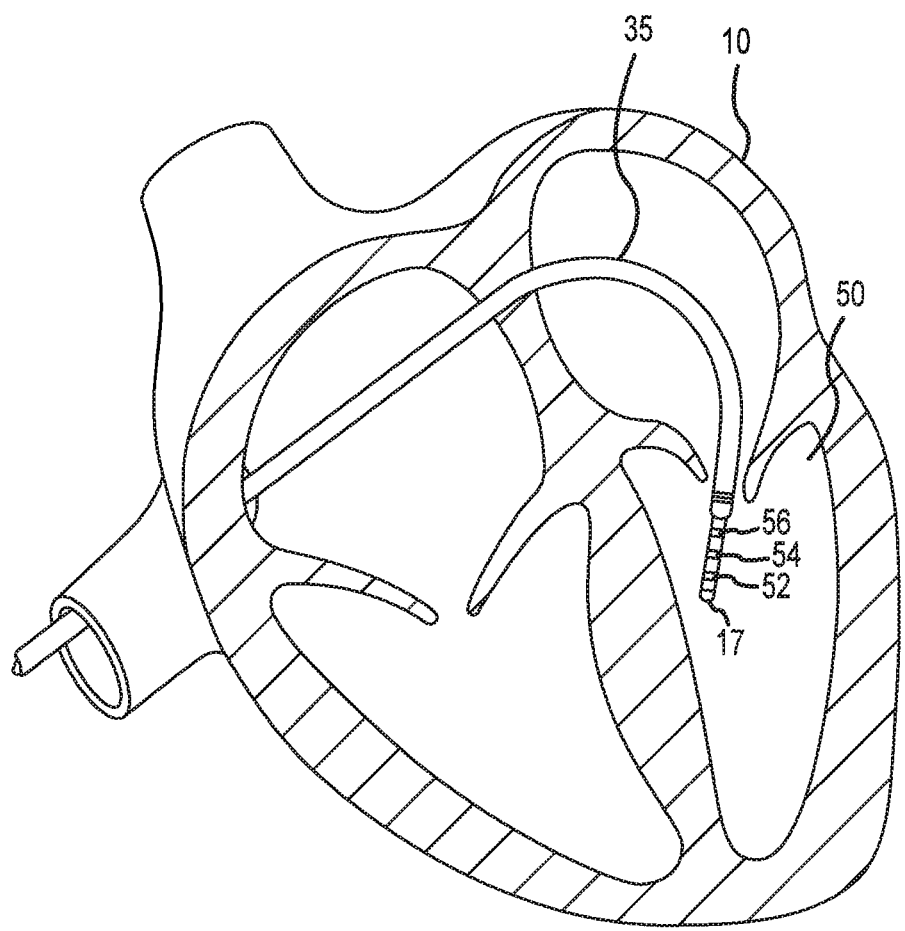
FIG. 3 depicts an exemplary multi-electrode catheter used in an electrophysiology study.

Likewise, it should be understood that catheter 13 (or multiple such catheters) typically introduced into the heart and/or vasculature of the patient via one or more introducers and using familiar procedures. For purposes of this disclosure, a segment of an exemplary multi-electrode catheter 13 is shown in FIG. 3. In FIG. 3, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the conduction velocity mapping techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the maps disclosed herein.

Returning now to FIG. 2, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one fir each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another such system that relies upon electrical fields. Other systems, however, may be used in connection with the present teachings, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

One methodology of mapping cardiac restitution will be explained herein with reference to the flowchart 400 of representative steps presented as FIG. 4. In some embodiments, for example, flowchart 400 may represent several exemplary steps that can be carried out by the computer 20 of FIG. 2 (e.g., by one or more processors 28) to identify and map cardiac restitution as described herein. It should be understood that the representative steps described below can be either hardware- or software-implemented. For the sake of explanation, the term "signal processor" is used herein to describe both hardware- and software-based implementations of the teachings herein.

In step 402, a plurality of electrophysiology ("EP") data points are acquired, for example using a multi-electrode catheter as described above. As described above, each EP data point will include location information and EP information including, without limitation, information regarding APD (or other cardiac repolarization activity data) and DI (or other quiescent interval data) at the relevant location.

In block 404, a user selects one of the collected EP data points to serve as the basis for defining a region of a cardiac surface. This point is referred to herein as an "anchor EP data point" or "intrinsic EP data point." Although the user can select any of the collected EP data points as the anchor EP data point, it is advantageous to select a sinus rhythm point as the anchor EP data point. It is also desirable for the anchor EP data point to be selected when the measuring catheter (e.g., catheter 13) is in stable contact with a point on the cardiac surface.

In block 406, a cluster of EP data points surrounding the anchor EP data point is identified. According to aspects of the instant disclosure, this EP data point cluster includes all EP data points that fall within a sphere surrounding the anchor EP data point, based, for example, upon their three dimensional Euclidean distance to the anchor EP data point. The radius of the sphere can be user-defined or preselected; in embodiments of the disclosure, the radius is 9 mm. In other embodiments, the radius of the sphere is greater or lesser than 9 mm.

Figure 5:
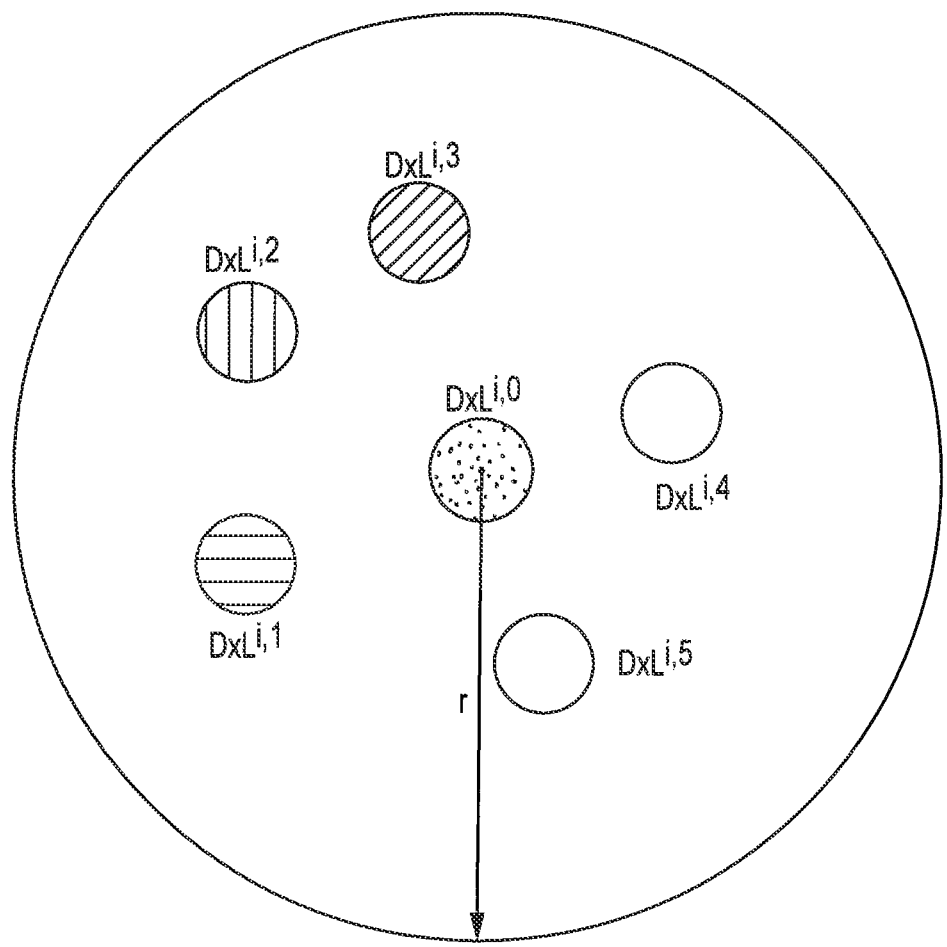
FIG. 5 illustrates the identification of an EP data point cluster according to embodiments of the instant disclosure.

The EP data point cluster defines a region i of the cardiac surface about the anchor EP data point. This is shown in two dimensions in FIG. 5. As shown in FIG. 5, the nomenclature $D \times L^{i,0}$ is used to denote the anchor EP data point for the $i^{th}$ region of the cardiac surface and the nomenclature $D \times L^{i,j}$ is used to denote the $j^{th}$ EP data point within the $i^{th}$ region of the cardiac surface (that is, the $j^{th}$ member of the EP data point cluster). It should also be understood that the EP data point cluster includes, and thus the $i^{th}$ region of the cardiac surface is defined by, a total of N EP data points; in FIG. 5, N=5.

Of course, it is contemplated that more than one anchor EP data point can be selected, which will result in the definition of a corresponding number of EP data point clusters and regions of the cardiac surface. This can also result in detecting EP data points that fall within the sphere of multiple anchor EP data points; this conflict can be resolved in various ways. For example, in some embodiments, the overlapping EP data point can be added to the region as to which its distance to the anchor EP data point is smallest. In other embodiments, the overlapping EP data point can be counted in both regions. In still other embodiments, the user can choose which region will include the overlapping EP data point.

A restitution curve is fit to the restitution data of the EP data point cluster in block 408. As described above, the restitution curve is an exponential curve and can have the form $y=f(x)=-a*e^{-\lambda x}+b$. As further described above, quiescent interval data (e.g., DI data) is used as the independent variable x, while cardiac repolarization activity data (e.g., APD) is used as the dependent variable y. a, b, and λ are referred to as "restitution parameters" and can be determined by optimizing a cost function. In particular, the cost function to be optimized can depend upon the type of clinical protocol applied (e.g., steady-state or dynamic).

For example, in the case of a steady-state protocol, the cost function can take the form $\min_\theta \Sigma_{j=1}^{N}(f(x^{i,j},\theta^i)-y^{i,j})^2$.

As another example, in the case of a dynamic protocol, the cost function can take the form $\min_\theta \Sigma_{m=0}^{K}(f(x^{i,j,m},\theta^i)-y^{i,j,m})^2$. In this instance, m denotes the $m^{th}$ beat, of a total of K beats, measured at the $j^{th}$ EP data point of the EP data point cluster.

In both cost functions described above, a, b, and λ are collectively denoted as parameter set θ. A bounded gradient-free optimization algorithm can be applied to optimize the parameter set θ, with bounds on a of [0.1, 1], on b of [0,1], and on λ of [0.1, 100].

Once the restitution curve is fit, one or more restitution metrics (e.g., maximum slope of restitution curve; asymptotic limit of restitution curve) can be identified. In the case of a steady-state protocol, the same restitution metric is applied to all EP data points within the region i (block 410). That is, for a steady-state restitution protocol, each and every EP data point within a given EP data point cluster will be assigned the same restitution metric for purposes of mapping cardiac restitution.

In the case of a dynamic protocol, on the other hand, the various EP data points in the EP data point cluster for a given region i can have different restitution metrics assigned thereto (block 412). In particular, a restitution curve can be fit to each EP data point individually over a series of beats.

In block 414, a graphical representation of the restitution metric can be displayed, for example on a three-dimensional model of the region of the cardiac surface.

FIG. 6A illustrates a representative restitution map 602 for a steady-state protocol. As shown in FIG. 6A, each EP data point 604 within a particular region (e.g., region 606), is assigned the same restitution metric. Greyscale or false color can be used to depict various values for the restitution metric on a model 608 of the cardiac surface.

FIG. 6B illustrates a representative restitution map 610 for a dynamic protocol. As shown in FIG. 6B, the EP data points 604 can have individualized restitution metrics. As with FIG. 6A, greyscale or false color can be used to depict various values for the restitution metric on model 608 of the cardiac surface.

Although several embodiments of this invention have been described above with a certain degree of particularity, those skilled in the art could make numerous alterations to the disclosed embodiments without departing from the spirit or scope of this invention.

Figure 4:
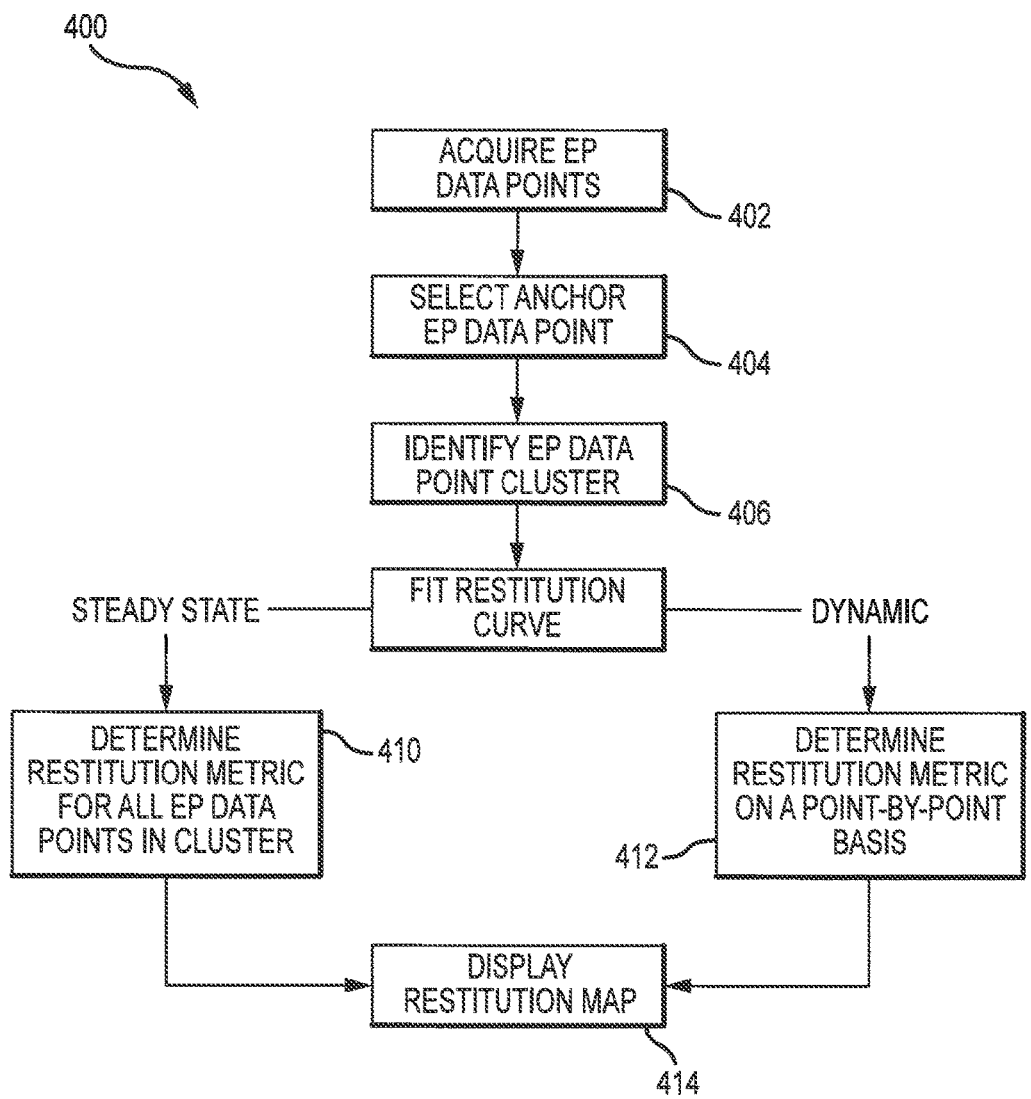
FIG. 4 is a flowchart of representative steps that can be followed to map cardiac restitution according to an embodiment of the disclosure.

For example, although methods of analyzing and mapping cardiac restitution are described primarily with reference to a single region of the cardiac surface, it should be understood that the steps described herein (e.g., as depicted in FIG. 4) can be repeated for multiple regions of the cardiac surface.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping cardiac restitution, comprising:
   receiving a plurality of electrophysiology ("EP") data points at a signal processor, each EP data point of the plurality of EP data points comprising location data and restitution data;
   receiving user input defining an anchor EP data point of the plurality of EP data points;
   identifying a subset of the plurality of EP data points forming an EP data point cluster about the anchor EP data point, wherein the EP data point cluster defines a region of a cardiac surface;
   fitting a restitution curve to the restitution data of the subset of the plurality of EP data points forming the EP data point cluster about the anchor EP data point; and
   identifying at least one restitution metric for the region of the cardiac surface from the restitution curve.

2. The method according to claim 1, further comprising outputting a graphical representation of the at least one restitution metric on a three-dimensional model of the region of the cardiac surface.

3. The method according to claim 1, wherein the restitution data comprises quiescent interval data, and wherein the quiescent interval data comprises one or more of DI data and cycle length data.

4. The method according to claim 1, wherein the restitution data comprises cardiac repolarization activity data, and wherein the cardiac repolarization activity data comprises one or more of APD data, ARI data, and EGM width data.

5. The method according to claim 1, wherein identifying a subset of the plurality of EP data points forming an EP data point cluster about the anchor EP data point comprises identifying a subset of the plurality of EP data points falling within a sphere centered at the anchor EP data point.

6. The method according to claim 5, wherein a radius of the sphere is user defined.

7. The method according to claim 5, wherein the sphere comprises a sphere of radius 9 mm.

8. The method according to claim 1, wherein fitting a restitution curve to the restitution data of the subset of the plurality of EP data points forming the EP data point cluster about the anchor EP data point comprises fitting an exponential restitution curve to the restitution data of the subset of the plurality of EP data points forming the EP data point cluster about the anchor EP data point.

9. The method according to claim 8, wherein the exponential restitution curve is defined by an equation $y=f(x)=-a*e^{-\lambda x}+b$, wherein x comprises quiescent interval data, y comprises cardiac repolarization activity data, and a, b, and $\lambda$ comprise a plurality of restitution parameters.

10. The method according to claim 9, wherein the plurality of restitution parameters a, b, and $\lambda$ are determined by optimizing a cost function.

11. The method according to claim 10, wherein the cost function is defined as $\min_\theta \Sigma_{j=1}^{N}(f(x^{i,j},\theta^i)-y^{i,j})^2$, wherein:
 i designates the region of the cardiac surface;
 j designates the $j^{th}$ EP data point, of a total of N EP data points, defining the region i of the cardiac surface;
 the restitution parameters a, b, and $\lambda$ are collectively designated $\theta$; and
  a is between 0.1 and 1, inclusive;
  b is between 0 and 1, inclusive; and
  $\lambda$ is between 0.1 and 100, inclusive.

12. The method according to claim 10, wherein the cost function is defined as $\min_\theta \Sigma_{m=0}^{K}(f(x^{i,j,m},\theta^i)-y^{i,j,m})^2$, wherein:
 i designates the region of the cardiac surface;
 j designates the $j^{th}$ EP data point defining the region i of the cardiac surface;
 m designates the $m^{th}$ beat, of a total of K beats, measured at the $j^{th}$ EP data point defining the region i of the cardiac surface;
 the restitution parameters a, b, and $\lambda$ are collectively designated $\theta$; and
  a is between 0.1 and 1, inclusive;
  b is between 0 and 1, inclusive; and
  $\lambda$ is between 0.1 and 100, inclusive.

13. The method according to claim 1, wherein the at least one restitution metric for the region of the cardiac surface comprises at least one of a maximum restitution curve slope and a restitution curve asymptotic limit.

14. The method according to claim 1, wherein identifying at least one restitution metric for the region of the cardiac surface from the restitution curve further comprises assigning an identical restitution metric for the region of the cardiac surface to the anchor EP data point and to each EP data point of the subset of the plurality of EP data points forming the EP data point cluster about the anchor EP data point.

15. A method of mapping cardiac restitution, comprising:
 acquiring a plurality of EP data points, each EP data point of the plurality of EP data points comprising location data, quiescent interval data, and cardiac repolarization activity data;
 inputting the plurality of EP data points to a signal processor, and, using the signal processor:
  identifying a subset of the plurality of EP data points forming an EP data point cluster;
  fitting a restitution curve to the quiescent interval data and the cardiac repolarization activity data of the subset of the plurality of EP data points forming the EP data point cluster; and
  identifying at least one restitution metric for the EP data point cluster using the restitution curve; and
 outputting a graphical representation of the identified at least one restitution metric for the EP data point cluster on a three-dimensional model of a region of a cardiac surface including the EP data point cluster.

16. The method according to claim 15, wherein fitting a restitution curve to the quiescent interval data and the cardiac repolarization activity data of the subset of the plurality of EP data points forming the EP data point cluster comprises fitting an exponential function using the quiescent interval data as the independent variable of the exponential function and the cardiac repolarization activity data as the dependent variable of the exponential function.

17. The method according to claim 15, wherein outputting a graphical representation of the identified at least one restitution metric for the EP data point cluster on a three-dimensional model of a region of a cardiac surface including the EP data point cluster comprises outputting a single graphical representation over an entirety of the region of the cardiac surface including the EP data point cluster.

18. The method according to claim 15, wherein identifying at least one restitution metric for the EP data point cluster using the restitution curve comprises identifying one or more of a maximum slope of the restitution curve and an asymptotic limit of the restitution curve.

19. A system for mapping cardiac restitution, comprising:
 a cardiac restitution analysis processor configured:
  to receive a plurality of EP data points, each EP data point of the plurality of EP data points comprising location data and restitution data, the restitution data comprising quiescent interval data and cardiac repolarization activity data;
  to identify a subset of the plurality of EP data points forming an EP data point cluster;
  to fit a restitution curve to the restitution data of the subset of the plurality of EP data points forming the EP data point cluster; and
  to identify at least one restitution metric for the EP data point cluster from the restitution curve.

20. The system according to claim 19, further comprising a mapping processor configured to generate and output a graphical representation of the at least one restitution metric for the EP data point cluster on a three-dimensional representation of a portion of a cardiac surface including the EP data point cluster.

* * * * *